United States Patent
Glick et al.

(10) Patent No.: US 8,124,140 B2
(45) Date of Patent: Feb. 28, 2012

(54) FLOWER REMEDY BEVERAGE AND METHOD OF MAKING

(75) Inventors: Orly Glick, Irvine, CA (US); Gilad Glick, Irvine, CA (US)

(73) Assignee: Maayan LLC, Irvine, CA (US)

( * ) Notice: Subject to any disclaimer, the term of this patent is extended or adjusted under 35 U.S.C. 154(b) by 128 days.

(21) Appl. No.: 12/587,030

(22) Filed: Sep. 30, 2009

(65) Prior Publication Data

US 2010/0196523 A1    Aug. 5, 2010

Related U.S. Application Data

(60) Provisional application No. 61/149,302, filed on Feb. 2, 2009.

(51) Int. Cl.
*A01N 65/00* (2009.01)
(52) U.S. Cl. ..................................................... 424/725
(58) Field of Classification Search ......................... None
See application file for complete search history.

(56) References Cited

U.S. PATENT DOCUMENTS

2009/0061029 A1 * 3/2009 Rouda ........................... 424/746

OTHER PUBLICATIONS

Shapiro, Jeffrey G. "The flower remedy book: A comprehensive guide to over 700 flower essences." 1999. pp. 193 and 196-197.

* cited by examiner

*Primary Examiner* — Michael Meller
(74) *Attorney, Agent, or Firm* — American Patent Agency PC; Daniar Hussain; Ryan Abbott

(57) ABSTRACT

A beverage and method of preparing a beverage comprising various combinations of flower essences designed for human consumption to treat emotional, mental and physical illnesses while providing hydration. In one illustrative embodiment of the method herein, a beverage is first formed by mixing a flower essence tincture with a diluent. A preservative flavoring and sweetener may also be added to the mixture. The beverage is then added to an empty container to form a filled container and then sealed to form a beverage product. The filled container may be sealed by, without limitation, applying a vacuum to the beverage therein, and/or capping an opening of the filled container. The capping may include applying a cap to the container, such as plastic or metallic cap. The container may be a plastic, glass or metallic bottle.

2 Claims, No Drawings

FLOWER REMEDY BEVERAGE AND METHOD OF MAKING

CROSS-RELATED REFERENCES

This application takes priority from provisional application Ser. No. 61/149,302 filed on Feb. 2, 2009.

FIELD OF THE INVENTION

The present invention relates to the field of flower essence-based remedies employing flower essences in a beverage configuration.

BACKGROUND ART

Homeopathy is a form of alternative medicine which is gaining acceptance and efficacy in the Western World. A central theme of homeopathy is to select a remedy, from naturally occurring substances, that addresses an illness both at a physical as well as metaphysical or psychological level.

Edward Bach, an English physician and homeopath, developed a set of homeopathic remedies in the 1930's based on a very small amount of flower material or essence, in a 50:50 solution of water and brandy. These remedies, while extremely dilute and absent of any characteristic, scent or taste of the flower plants, have been used to treat a variety of conditions, ailments and illnesses. Further, consumers now look to flower essence remedies for proactively maintaining a healthy state or positive outlook.

One of the most popular of these remedies is known as the Rescue Remedy: a combination of an equal amount of each of Rock rose, Impatiens, Clematis, Star of Bethlehem and Cherry Plum for the flower essence component, mixed with water and an alcohol-based dilution agent. This solution is targeted toward stress, anxiety and panic. Several companies produce similar solutions using several of the same flower essences. Such remedies and other flower essence solutions are typically administered orally as a spray or as a concentrate in the form of several drops of the solution, and are not provided with a sufficient diluent to hydrate a consumer of the product.

Consumers of flower essence remedies, however, are closely aligned with an explosive growth in the bottled water and energy drinks market. The former market may focus on brand development, in which each of the various branded bottled water vendors seeks an advantage—from exotic locations to the mineral or carbonation content of their water. The latter market typically involves water that is sweetened with one or more of a variety of sweeteners, and having vitamins, minerals or other plant-based substance as an additive. However, there currently is no known drink for human consumption that relies on a set of flower essences such as the list of essences identified by Dr. Bach, and which can also hydrate a consumer.

SUMMARY OF THE INVENTION

This application discloses various compositions in the form of commercially-available beverages, each containing a specific combination and amount of flower essences to provide the general advantages of the flower essence remedies, without needing a diagnosis or specific relationship between the remedies and a condition.

Although a small sample of some of the most well-known flower essences is listed herein, there are literally hundreds of flower essences that are known for the treatment of various mental, emotional or physical symptoms. Therefore, a published book having a more comprehensive listing of flower essences and symptoms they are used to treat is incorporated herein by reference as if fully set forth herein. This book is entitled "The Flower Remedy Book—A Comprehensive Guide To Over 700 Flower Essences" by Jeffrey Garson Shapiro, copyright 1999, published by North Atlantic Books of Berkeley, Calif.

The details of various embodiments are sent forth in the accompanying description below. Other features and advantages will be apparent from the following description and from the claims.

DETAILED DESCRIPTION OF PREFERRED EMBODIMENTS

The present invention relates to the form of a beverage for commercial consumption, containing flower essences mixed with a volume of a diluent, such as water, and/or other mixing agent, and/or a preservative, such as alcohol. Other elements can be used, such as flavorings or sweeteners. The flower essences are preferably included as a tincture, i.e., fluid or solid forms of the flower essences in an agent such as alcohol. The tincture forms the basic delivery mechanism of the flower essences to the diluent for forming the beverage.

Table 1 below is a list of flowers and their Latin designations for use in a tincture:

TABLE 1

Agrimony - *Agrimonia eupatoria*
Aspen - *Populus tremula*
Beech - *Fagus sylvatica*
Centaury - *Centaurium Umbellatum*
Cerato - *Ceratostigma Willmottiana*
Cherry Plum - *Prunus Cerasifera*
Chestnut Bud - *Aesculus Hippocastanum*
Chicory - *Cichorium intybus*
Clematis - *Clematis vitalba*
Crab Apple - *Malus pumila*
Elm - *Ulmus procera*
Gentian - *Gentiana amarella*
Gorse - *Ulex eruopoeus*
Heather - *Calluna vulgaris*
Holly - *Ilex aquifolium*
Honeysuckle - *Lonicera caprifolium*
Hornbeam - *Carpinus Betulus*
Impatiens - *Impatiens glandulifera*
Larch - *Mimulus guttatus*
Mustard - *Sinapis arvensis*
Oak - *Quercus robur*
Olive - *Olea europoea*
Pine - *Pinus sylvestris*
Red Chestnut - *Aesculus carnea*
Rock Rose - *Helianthemum nummularium*
Rock Water -
Scleranthus - *Scleranthus annuus*
Star of Bethlehem - *Ornithogalum umbetlatum*
Sweet Chestnut - *Castanea sativa*
Vervain - *Verbena officinalis*
Vine - *Vitis vinifera*
Walnut - *Juglans regia*
Water Violet - *Hottonia palustris*
White Chestnut - *Aesculus hippocastanum*
Wild oat - *Bromus ramosus*
Wild Rose - *Rosa canina*
Willow - *Salix vitellina*

Table 2 below is a list of many of the flower essences and the associated emotional or spiritual condition to which they are thought to provide a perceived remedy:

TABLE 2

Agrimony - mental torture behind a cheerful face
Aspen - fear of unknown things
Beech - intolerance
Centaury - inability to say 'no'
Cerato - lack of trust in one's own decisions
Chamomile - distraught emotions
Cherry Plum - fear of the mind giving way
Chestnut Bud (made with horse chestnut buds) - failure to learn from mistakes
Chicory - selfish, possessive love
Clematis - dreaming of the future without working in the present
Crab Apple - cleansing remedy, also for self-hatred
Elm - overwhelmed by responsibility
Gentian - discouragement after a setback
Gorse - hopelessness and despair
Heather - self-centeredness and self-concern
Holly - hatred, envy and jealousy
Honeysuckle - living in the past
Hornbeam - procrastination, tiredness at the thought of doing something
Impatiens - impatience
Larch - lack of confidence and self-esteem
Mimulus - fear of known things
Mustard - deep gloom for no reason
Oak - the plodder who keeps going past the point of exhaustion
Olive - exhaustion following mental or physical effort
Pine - guilt
Red Chestnut (a type of horse chestnut) - over-concern for the welfare of loved ones
Rock Rose - terror and fright
Rock Water - self-denial, rigidity and self-repression
Scleranthus - inability to choose between alternatives
Star of Bethlehem - shock
Sweet Chestnut - extreme mental anguish, when everything has been tried and there is no light left
Vervain - over-enthusiasm
Vine - dominance and inflexibility
Walnut - protection from change and unwanted influences
Water Violet - pride and aloofness
White Chestnut (made with horse chestnut blossoms) - unwanted thoughts and mental arguments
Wild oat - uncertainty over one's direction in life
Wild Rose - drifting, resignation, apathy
Willow - self-pity and resentment Each remedy may be used alone, or in combination with other remedies. Each flower essence may be used in a specific quantity in a beverage for remedying a specific general emotional, physical or spiritual state. Accordingly, there are an unlimited number of matrices of remedies/combinations of remedies that are provided by specific beverage compositions.

In one particular implementation, as an example, and in accordance with the tables above, a RELAX beverage may be formed as a remedy for stress relief. The RELAX beverage includes a tincture having Elm, White Chestnut, Rock Rose, Impatiens, Vervain, Chamomile. The flower essences in the tincture of the RELAX beverage can be provided in any combination or proportions, such as in equal volumetric amounts. Or, there may be a specific combination or proportion of the flower essences, or even different flower essences.

For example, an alternative RELAX beverage includes a tincture having flower essences of Impatiens, Elm, White Chestnut and Mustard. Yet another alternative RELAX beverage includes a tincture having flower essences of Mimulus, Cherry Plum, Aspen and Gorse. These alternative beverages, while specifically formulated for stress relief, may have varying effects on the causes and response to different stresses being experienced by the consumer. Therefore, the remedies are actually different remedies that are directed to similar objectives.

In other specific examples, a CONFIDENCE beverage includes a tincture having flower essences of Cerato and Larch. A FOCUS beverage includes a tincture having flower essences of Cerato, Scleranthus, Elm, Clematis and White Chestnut. A SEPARATION ANXIETY beverage includes a tincture having flower essences of Chicory, Red Chestnut and Walnut and a HAPPY beverage includes a tincture having flower essences of Holly, Sweet Chestnut, Gentian, Gorse, Wild Rose and Mustard.

In order to maintain a reasonable shelf-life and thereby prolong the usefulness of a beverage, a preservative can be added to the beverage to preserve freshness of the flower essences and/or preserve the freshness of the water. In some implementations, the preservative is based on an alcohol. Other preservatives may be suitable.

In some alternatives, a beverage includes 1 to 30 drops of a flower essence or various combinations of flower essences. Each drop is a standard drop of water, which is commonly understood to be 0.05 milliliters of volume, 0.025 grams of mass. A beverage product may include 6 to 24 fluid ounces of a mixture of diluent, flower essence tincture and a preservative. Alternatively, a beverage product may contain fewer than 6 fluid ounces, or more than 24 fluid ounces of the mixture.

In some implementations, a beverage product is made according to a process. The process includes the steps of providing an empty container and filling the empty container with a beverage to form a filled container. In accordance with one implementation, a process of making a beverage product includes filling the empty container with a diluent, such as water, to form a filled container. The process further includes adding a flower essence tincture to the filled container and sealing the mixture of flower essence tincture and diluent within the filled container to make the beverage product.

In accordance with an alternative implementation, a beverage is first formed by mixing a flower essence tincture with a diluent. A preservative may also be added to the mixture. The beverage is then added to an empty container to form a filled container and then sealed to form a beverage product. The filled container may be sealed by, without limitation, applying a vacuum to the beverage therein, and/or capping an opening of the filled container. The capping may include applying a cap to the container, such as plastic or metallic cap. The container may be a plastic, glass or metallic bottle with an opening.

Another process of making a beverage product includes repeating the process for making a single beverage product, in a serial or parallel fashion, for making a large number of beverage products. The large number of beverage products are suitable for realizing an economy of scale in making the beverage products and for activities such as wholesale or retail distribution of the beverage products and for mass consumption of the flower essence tincture by delivery via the diluent from the beverage products.

Although examples of the present invention have been presented herein by way of illustration, it will be apparent that there are many other flower essences available that are safe, practical and effective for treating many symptoms. Therefore, the disclosure herein has incorporated by reference a published book entitled: "The Flower Remedy Book—A Comprehensive Guide To Over 700 Flower Essences" by Jeffrey Garson Shapiro, copyright 1999.

Although several illustrative embodiments have been described in detail above, other modifications are possible. The process flows described above do not require the particular flower essences, the step order shown, or sequential order, to achieve desirable results. Other embodiments may be within the scope of the following claims.

We claim:

1. A beverage, consisting essentially of:
   a diluent comprising between 95% to 99.9998% by volume water; and
   a tincture comprising between 0.0002% to 5% by volume flower essence extracts from white chestnut, impatiens, and rock rose.

2. A beverage, consisting essentially of:
   a diluent comprising between 95% to 99.9998% by volume water;
   a tincture comprising between 0.0002% to 5% by volume flower essence extracts from white chestnut, impatiens, and rock rose; and
   ethanol.

* * * * *